US012569642B2

(12) United States Patent
Fiske

(10) Patent No.: US 12,569,642 B2
(45) Date of Patent: Mar. 10, 2026

(54) CHILD SLEEP CLOCK

(71) Applicant: FISKETECH, LLC, McLean, VA (US)

(72) Inventor: David Fiske, McLean, VA (US)

(73) Assignee: FISKETECH, LLC, McLean, VA (US)

( * ) Notice: Subject to any disclaimer, the term of this patent is extended or adjusted under 35 U.S.C. 154(b) by 1376 days.

(21) Appl. No.: 17/204,509

(22) Filed: Mar. 17, 2021

(65) Prior Publication Data

US 2021/0290892 A1    Sep. 23, 2021

Related U.S. Application Data

(60) Provisional application No. 62/991,321, filed on Mar. 18, 2020.

(51) Int. Cl.
 A61M 21/02     (2006.01)
 A61M 21/00     (2006.01)
 (Continued)

(52) U.S. Cl.
 CPC ............. A61M 21/02 (2013.01); G04G 5/002 (2013.01); G04G 9/10 (2013.01); G04G 13/02 (2013.01);
 (Continued)

(58) Field of Classification Search
 CPC .......... A61M 21/02; A61M 2021/0044; G04G 5/002; G04G 9/10; G04G 13/02;
 (Continued)

(56) References Cited

U.S. PATENT DOCUMENTS 7,048,433 B1 * 5/2006 Bhavnani ............. G04G 17/086
                                                  368/76
10,437,200 B1 * 10/2019 Ostler .................. G04G 9/0017
 (Continued)

FOREIGN PATENT DOCUMENTS

EP        2033681 A1 *  3/2009  ............ A61M 21/02
GB        2442757 A  *  4/2008  ............ G04G 9/022

OTHER PUBLICATIONS

Choosing a debug/programming connector for a microcontroller, PartsBox Blog, Mar. 27, 2019, accessed online on Apr. 24, 2025 at URL: https://partsbox.com/blog/choosing-a-debug-programming-connector-2019.html (see attached) (Year: 2019).*
 (Continued)

*Primary Examiner* — Sunita Reddy
(74) *Attorney, Agent, or Firm* — XSENSUS LLP

(57)        ABSTRACT
A sleep training clock can be configured to assist in sleep training. The sleep training clock is shaped like a robot having a face, a torso, and two legs; two LEDs disposed in the face and three LEDs disposed in the torso; and a digital clock face disposed in the torso. Additionally, circuitry for performing sleep training is configured to determine whether the electronic device is in a wake state and turn on the two LEDs disposed in the face and turn off the three LEDs disposed in the torso in response, determine whether the electronic device is in a sleep state and turn off the two LEDs disposed in the face and turn on the three LEDs disposed in the torso in response.

15 Claims, 12 Drawing Sheets

(51) Int. Cl.
| | |
|---|---|
| *G04G 5/00* | (2013.01) |
| *G04G 9/10* | (2006.01) |
| *G04G 13/02* | (2006.01) |
| *G04G 21/04* | (2013.01) |

(52) U.S. Cl.
CPC ..... *G04G 21/04* (2013.01); *A61M 2021/0044* (2013.01)

(58) Field of Classification Search
CPC ........ G04G 21/04; G04G 11/00; G04G 17/04; G04G 13/026
USPC ...................................................... 600/26–28
See application file for complete search history.

(56)                References Cited

U.S. PATENT DOCUMENTS

| | | | | | |
|---|---|---|---|---|---|
| 2002/0075156 | A1* | 6/2002 | Soker | .................... | G06F 11/324 |
| | | | | | 714/E11.184 |
| 2002/0081937 | A1* | 6/2002 | Yamada | ................. | A63H 11/00 |
| | | | | | 446/175 |
| 2005/0117458 | A1* | 6/2005 | Claessens | ................ | G04G 9/02 |
| | | | | | 368/223 |
| 2008/0157981 | A1* | 7/2008 | Clair | ........................ | G09B 5/00 |
| | | | | | 340/500 |
| 2008/0192580 | A1* | 8/2008 | Larian | .................... | G04C 23/00 |
| | | | | | 368/10 |
| 2008/0232199 | A1* | 9/2008 | Shafton | ................... | G04F 1/005 |
| | | | | | 368/107 |
| 2009/0077203 | A1* | 3/2009 | Janik | ...................... | G04G 11/00 |
| | | | | | 709/219 |
| 2009/0079561 | A1* | 3/2009 | Nelson | ................... | G04C 19/02 |
| | | | | | 340/540 |
| 2010/0052918 | A1* | 3/2010 | Walker | .............. | A61M 15/0083 |
| | | | | | 340/575 |
| 2010/0296370 | A1* | 11/2010 | Holmes | ................... | G04F 1/005 |
| | | | | | 368/73 |
| 2014/0228622 | A1* | 8/2014 | Patel | ........................ | A63H 3/28 |
| | | | | | 600/27 |
| 2015/0224417 | A1* | 8/2015 | Richardson | .............. | A63H 3/28 |
| | | | | | 446/485 |
| 2016/0279381 | A1* | 9/2016 | Ahne | ...................... | A61B 5/486 |
| 2016/0379107 | A1* | 12/2016 | Li | ........................ | B25J 11/0005 |
| | | | | | 706/11 |
| 2018/0214784 | A1* | 8/2018 | Klein | ........................ | A63H 3/02 |
| 2019/0366558 | A1* | 12/2019 | Gupta | .................... | B25J 11/009 |
| 2020/0058387 | A1* | 2/2020 | Stahel | .................... | G16H 20/30 |
| 2020/0077495 | A1* | 3/2020 | Harrison | ............... | H05B 47/19 |
| 2020/0372829 | A1* | 11/2020 | Ostler | ................. | G04G 9/0064 |
| 2022/0155731 | A1* | 5/2022 | Lai | ........................ | G04G 13/021 |
| 2022/0241985 | A1* | 8/2022 | Scherer | ............... | B25J 11/0015 |

OTHER PUBLICATIONS

A Guide To NTP Clocks and Networked Time Displays, TimeTools by Editorial Staff, Aug. 13, 2018, accessed online on Apr. 25, 2025 at URL: https://timetoolsltd.com/network-clocks/a-guide-to-ntp-clocks-and-networked-time-displays/ (see attached) (Year: 2018).*

* cited by examiner

300

Back Side

300

Probe Side

715

CHILD SLEEP CLOCK

CROSS-REFERENCE TO RELATED APPLICATION

This application claims the benefit of U.S. Provisional Application No. 62/991,321, filed Mar. 18, 2020, which is incorporated herein by reference in its entirety.

FIELD OF THE DISCLOSURE

The present disclosure relates to a clock, and more specifically to a clock for sleep training.

BACKGROUND

Alarm clocks for young children can be configured to assist with sleep training. For adults, alarm clocks simply help determine when it's time to wake up. However, young children often do not need prompting to wake up. In fact, the opposite is true. Young children typically need guidance about staying in bed instead. In other words, sleep training clocks can assist young children in determining when they should stay in bed and when they are allowed to get out of bed.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

SUMMARY

According to an aspect of the present disclosure, a clock for sleep training is described.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed subject matter. However, it will be apparent to those skilled in the art that embodiments may be practiced without these specific details. In some instances, well-known structures and components may be shown in block diagram form in order to avoid obscuring the concepts of the disclosed subject matter.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features. Additionally, it is to be understood that terms such as "left," "right," "top," "bottom," "front," "rear," "side," "height," "length," "width," "upper," "lower," "interior," "exterior," "inner," "outer," and the like that may be used herein, merely describe points of reference and do not necessarily limit embodiments of the disclosed subject matter to any particular orientation or configuration.

Figure 1B:
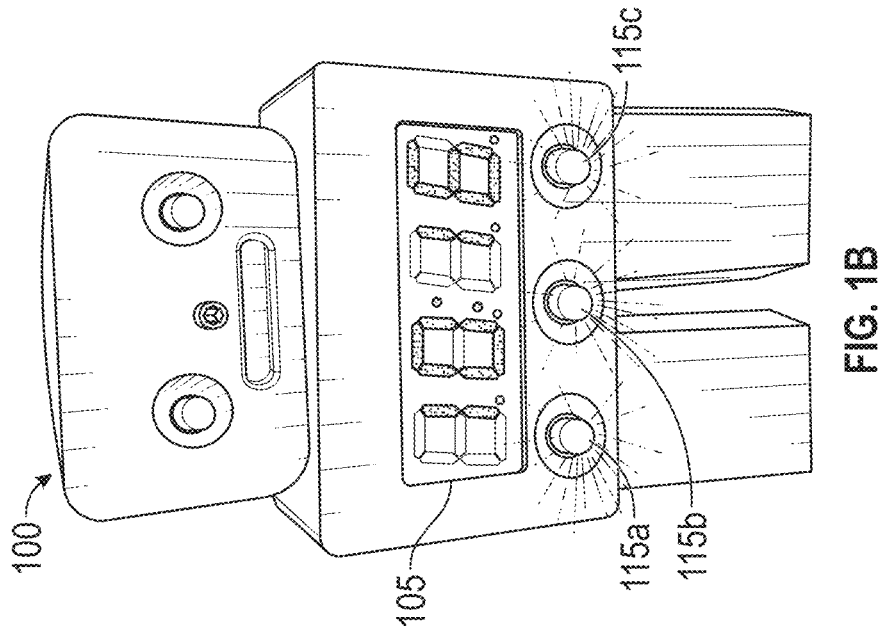
FIG. 1B illustrates a front view of a sleep training clock in a sleep state according to one or more aspects of the disclosed subject matter.
Figure 1A:
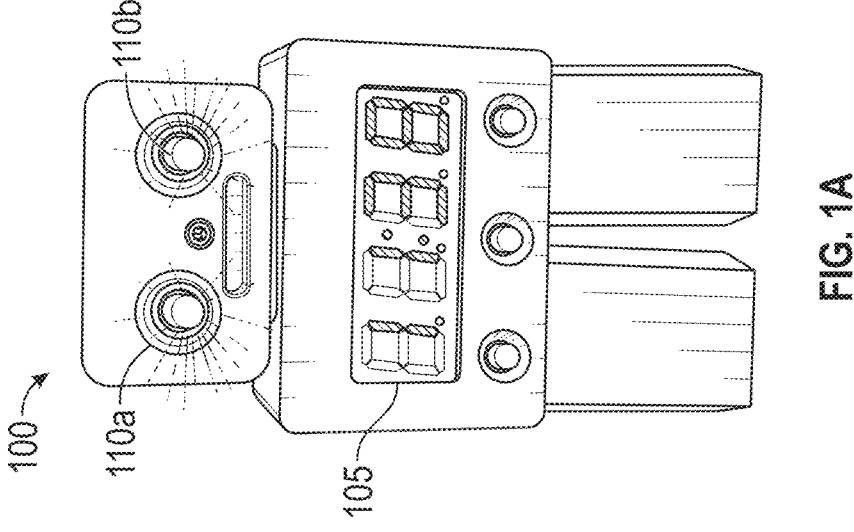
FIG. 1A illustrates a front view of a clock for sleep training in a wake state according to one or more aspects of the disclosed subject matter.

FIG. 1A and FIG. 1B illustrate a sleep training clock 100. Generally, a sleep training clock is a device that shows the current time, as a standard clock, and also provides some other visual cue that indicates to children whether or not they are allowed to leave bed. The visual cue is meant to be simple enough that young children who cannot yet understand how to read time can understand the cue alone. The sleep training clock 100 can include a digital display 105 showing the current time and a system of lights (110a, 110b and 115a, 115b, and 115c) that indicate to younger children whether it is time to sleep or if they are permitted to wake up and leave their rooms.

In one aspect, the sleep training clock 100 can have an external appearance of a robot. It should be appreciated that sleep training clock and robot can be used interchangeably herein. The robot (i.e., sleep training clock 100) can have lights arranged as eyes 110a, 110b and a belt 115a, 115b, and 115c, with only the eyes 110a-b illuminated when the child can leave bed and only the belt 115a-c illuminated when the child must remain in bed. The design is meant to give the impression that the robot itself is awake (e.g., eyes "open") or asleep (e.g., eyes "closed") at the appropriate times.

FIG. 1A illustrates a front view of the sleep training clock 100 in a wake state according to one or more aspects of the disclosed subject matter. For example, the wake state can correspond to the lights of the robot's eyes (i.e., lights 110a-b) being illuminated based on a predetermined set time. For example, a wake time can be set for 7:00 am such that the lights of the robot's eyes are not illuminated until 7:00 am. Before 7:00 am, the lights of the robot's belt will be illuminated. The same can be performed for a nap during the day such that the robot's belt will be illuminated from 3:00 μm to 4:00 pm indicating a sleep state, and at 4:00 pm the robot's belt will turn off and the robot's eyes will be illuminated indicating a wake state.

FIG. 1B illustrates a front view of the sleep training clock 100 in a sleep state according to one or more aspects of the disclosed subject matter. For example, the sleep state can correspond to the lights of the robot's belt (i.e., lights 115a-c) being illuminated.

More specifically, the sleep training clock 100 has a digital clock face (e.g., digital display 105) showing in a chest area (e.g., torso) of the robot and five additional LEDs placed into two groups: 1) two LEDs (e.g., lights 110a-b) as eyes located in a face of the robot, and three LEDs (e.g., lights 115a-c) configured to represent a belt positioned under the clock display and above the legs. Each of the five LEDs (e.g., lights 110a-b and 115a-c) can be controlled via firmware separately such that each can be independently turned on or off and the color of the LED can be changed according to situational context or in response to user preferences. In one aspect, the clock face can be a prefabricated display consisting of four seven-segment characters separated by a colon and with decimal point available after each character. In such display, each segment (including the colon and the decimals) includes an LED that can be individually controlled by driver circuitry. The clock face, in addition to showing the time, can display text and other information according to rules defined by the software in response to external events and user controls. Additionally, the clock face can have a coloring corresponding to yellow, green, white, red, or blue, for example.

A back side of the robot (i.e., opposite the front of the robot) can be closed by a cover attached by screws to the front casing. The cover can include holes that allow access to a USB receptacle, two push buttons, one two-element dual in-line package (DIP) switch, and one slide switch. The USB receptacle can be used to provide power to the device. In one aspect, the USB receptacle can be positioned in a foot of the robot and held securely by a component designed to hold the USB receptacle in place in the foot. The component screws into the main body of the robot, which holds the USB receptacle when it is mated or unmated, and screws to the PCB to which the USB receptacle is mounted. The push buttons, DIP switch, and slide switch allow the user to manually control functions of the device in a way that is determined by the firmware running on the device.

Figure 2A:
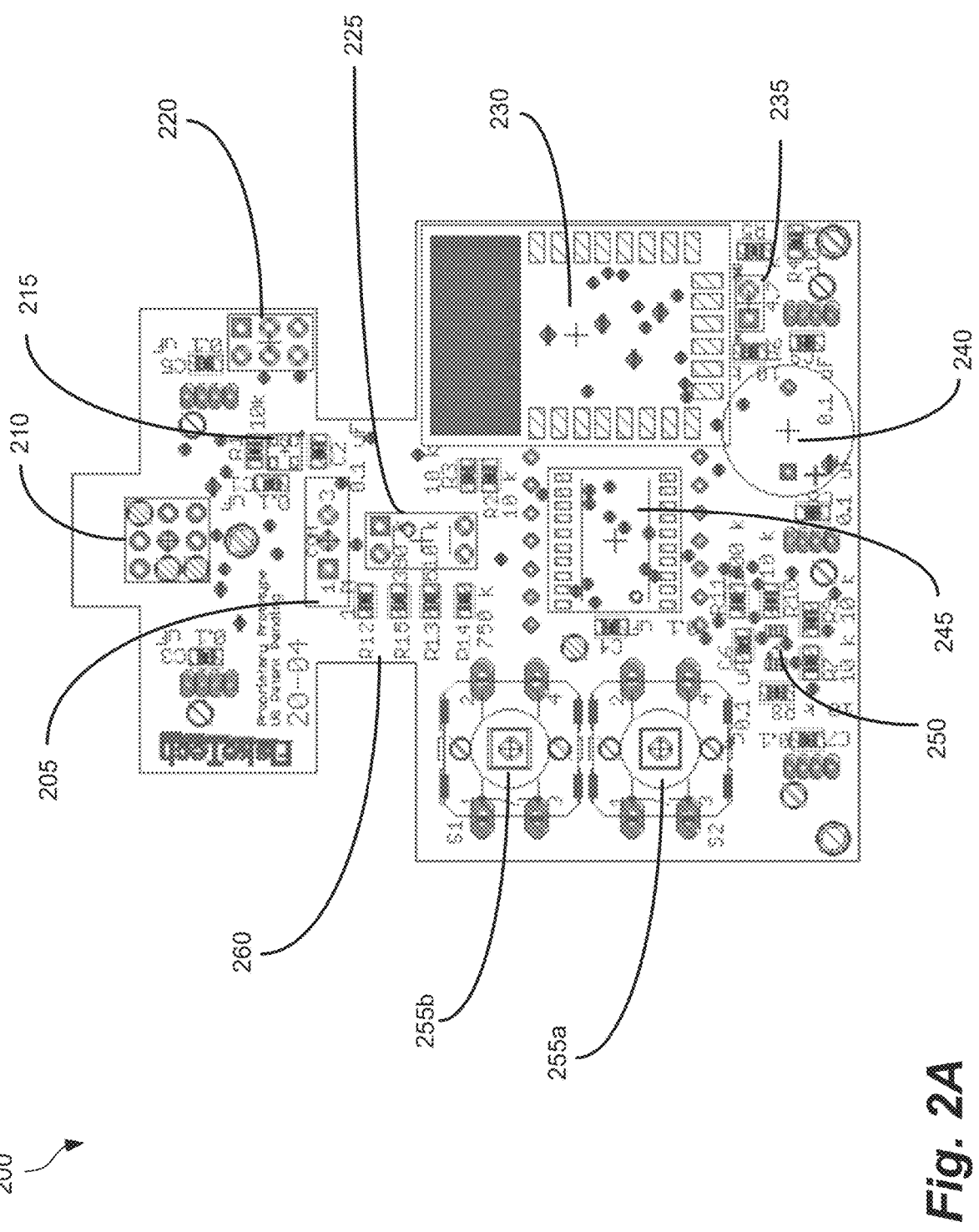
FIG. 2A illustrates a front view of an assembled printed circuit board (PCB) for the sleep training clock according to one or more aspects of the disclosed subject matter.

FIG. 2A illustrates a front view of an assembled printed circuit board (PCB) 200 for the sleep training clock 100 according to one or more aspects of the disclosed subject matter.

Figure 2B:
FIG. 2B illustrates a back view of the assembled PCB for the sleep training clock according to one or more aspects of the disclosed subject matter.

FIG. 2B illustrates a back view of the assembled PCB 200 for the sleep training clock 100 according to one or more aspects of the disclosed subject matter.

The PCB 200 in FIGS. 2A and 2B can represent one or more PCBs on which electronics inside the sleep training clock 100 are mounted. The electronics mounted to the PCB 200 of the sleep training clock 100 can include a USB receptacle, the LEDs (eyes 110a, 110b and belt 115a-c), and the clock face 105. In one aspect, the USB receptacle is not mounted directly to the PCB 200, but it can be connected to the PCB 200 at connection points 235 via two wires running from a USB receptacle positioned in a leg of the robot. Additionally, the push buttons 255a and 255b, DIP switch 225, and slide switch 205 mentioned above can be mounted to the PCB 200. The PCB 200 can also include a processor 230 (e.g., microcontroller) that runs firmware controlling the overall operation of the sleep training clock 100 and that interacts with other electronic components of the device through digital, general purpose input/output (GPIO) pins and analog pins that can read or write voltages on a continuous spectrum. Some of the pins may be configured for UART, i2c, or SPI communication. In one aspect, the design can use ESP-8266 pre-packaged with a Wi-Fi capability. Additionally, a Wi-Fi transmitter/receiver, power conversion 215 (5.0V to 3.3 V), a voltage divider 260 attached to the DIP switch such that each configuration of the DIP switch will result in a unique voltage that can be read by an analog pin to determine the configuration of the switch, and an LED driver chip 245 that controls the individual segments on the clock face and interacts with the microcontroller 230 via the i2c protocol can also be mounted to the PCB 200. Further, the PCB 200 can include level conversion circuitry 250 for i2c for components working on 5.0 V and 3.3 V, a piezo-electric buzzer 240, a programming port 210 that allows a temporary physical connection to be made between the PCB (and components mounted thereon) and an external computer and that is used to provide the initial firmware upload to the microcontroller and to run test suites on a device for quality control, and various resistors and capacitors configured to support the above components as well as wires, connectors, and PCB traces that make appropriate connections between components. The PCB 200 can also include a debugging port 220.

Figure 3B:
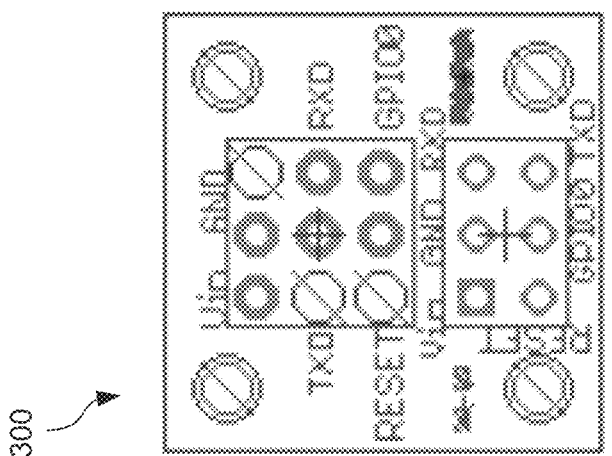
FIG. 3B illustrates a back side of the probe device that mates with the programming port on the PCB according to one or more aspects of the disclosed subject matter.
Figure 3A:
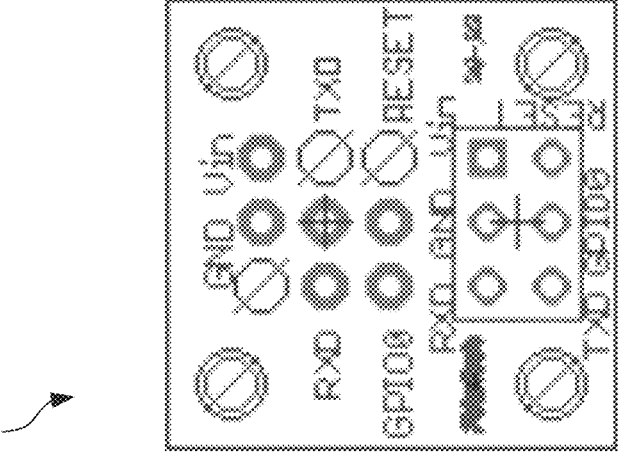
FIG. 3A illustrates a probe side of a probe device that mates with the programming port on the PCB according to one or more aspects of the disclosed subject matter.

FIG. 3A illustrates a probe side of a probe device 300 that mates with the programming port 210 on the PCB 200 according to one or more aspects of the disclosed subject matter.

FIG. 3B illustrates a back side of the probe device 300 that mates with the programming port 210 on the PCB 200 according to one or more aspects of the disclosed subject matter.

Figures 4A, 4B:
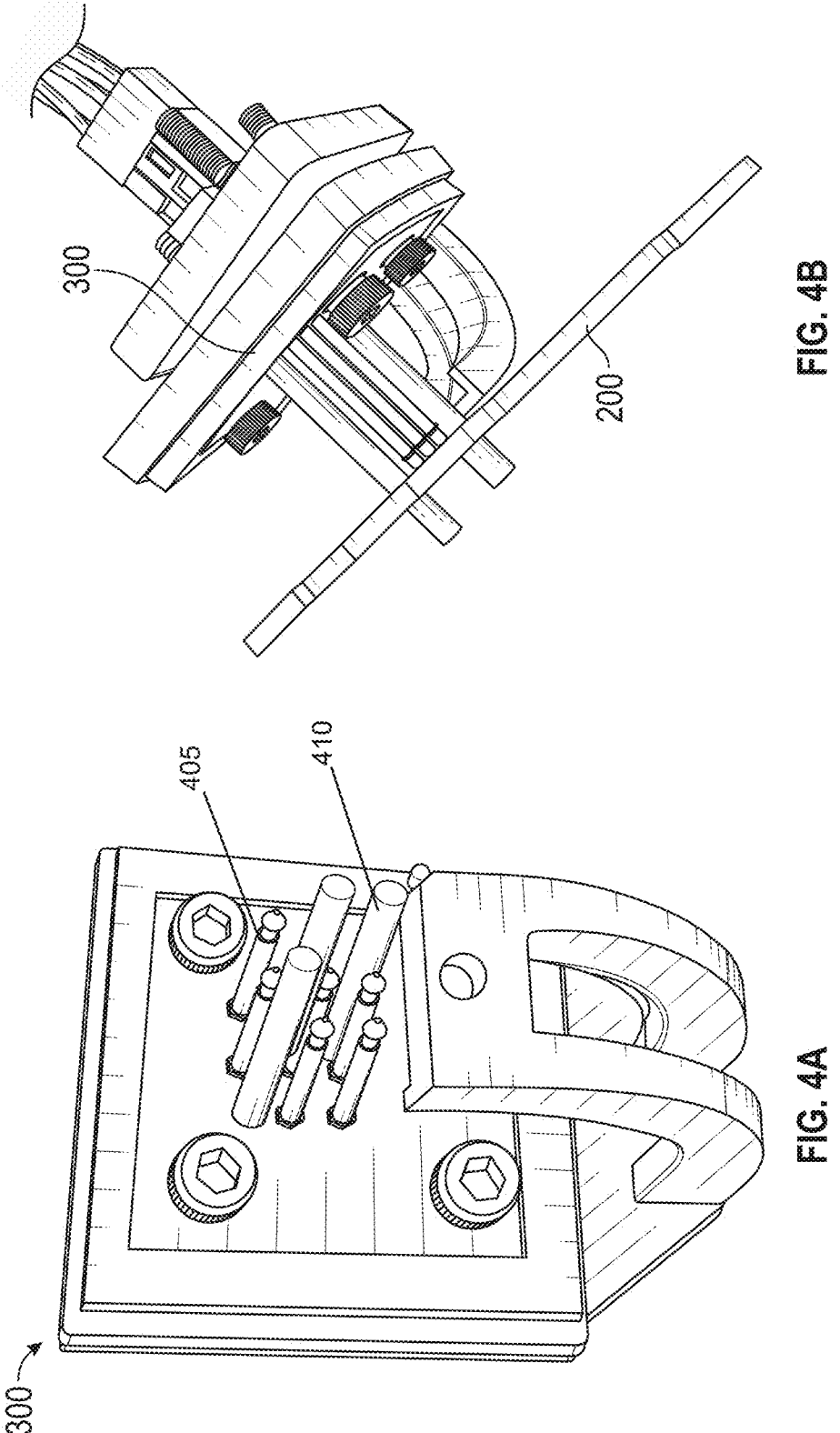
FIG. 4A illustrates an assembled probe device mounted into a test brace according to one or more aspects of the disclosed subject matter.
FIG. 4B illustrates a side view of the probe device when mating with the PCB according to one or more aspects of the disclosed subject matter.

FIG. 4A illustrates an assembled probe device 300 mounted into a test brace according to one or more aspects of the disclosed subject matter.

FIG. 4B illustrates a side view of the probe device 300 when mating with the PCB 200 according to one or more aspects of the disclosed subject matter.

Figure 4C:
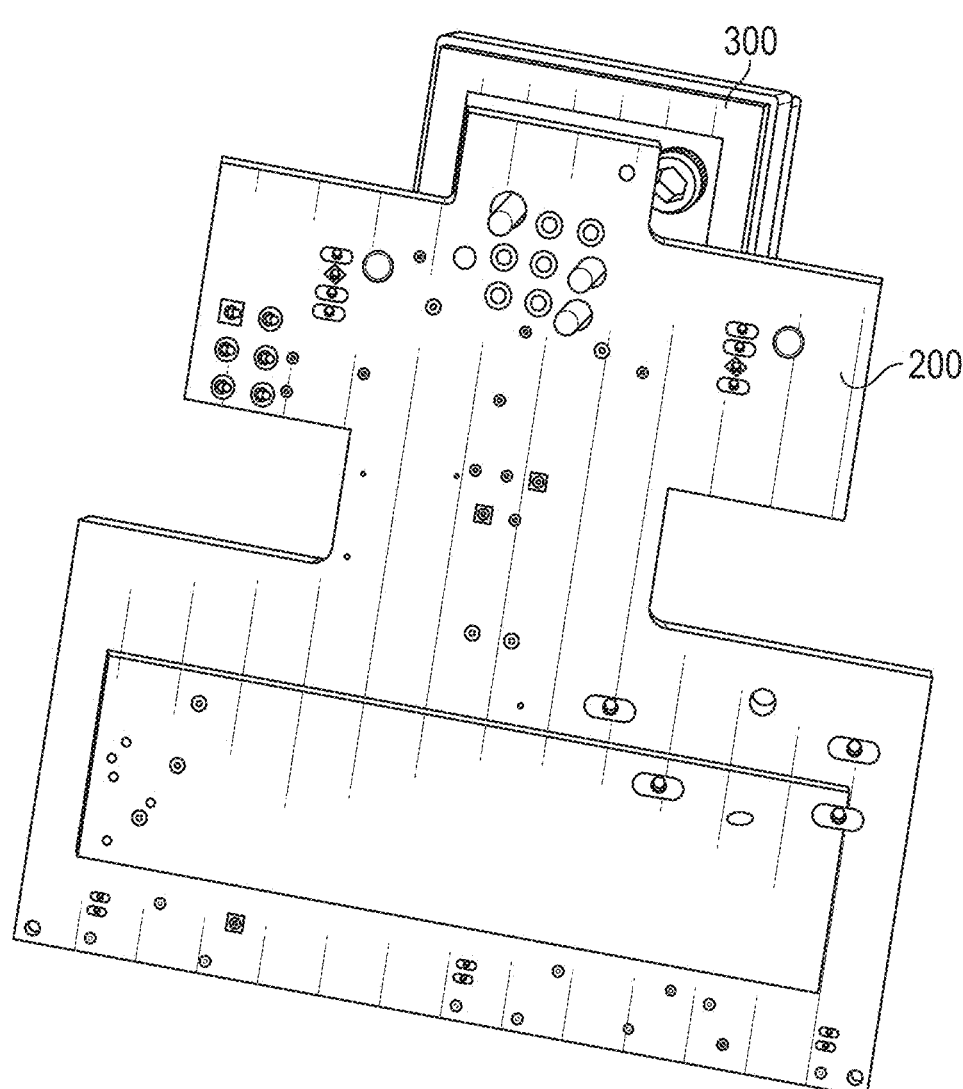
FIG. 4C illustrates the probe device as seen through the PCB when mating according to one or more aspects of the disclosed subject matter.

FIG. 4C illustrates the probe device 300 as seen through the PCB 200 when mating according to one or more aspects of the disclosed subject matter.

Referring to FIGS. 3A-B and FIGS. 4A-C, complementary to the programming port 210 on the PCB 200, as described above, is a probe device 300 that mates with it. The probe device 300 includes a PCB to which six "pogo" style pins (e.g., pin 405) are attached to make temporary contact with corresponding locations on the programming port 210. This establishes electrical connections between the electronics on the PCB and an external computer that is used to provide initial programming to the microcontroller. The probe device 300 also has three non-conducting pegs (e.g., peg 410) of larger diameter that fit into corresponding holes in the programming port 210. The six pins and three pegs are arranged in a 3×3 pattern with the pegs taking positions that only allow the probe device 300 to mate with the programming port 210 from one side of the board and in one orientation. By making the pegs slightly longer than the pins, this reduces or eliminates the potential for the pins on the probe to contact the wrong pads on the programming port 210, which in turn protects both the device to be programmed and the computer uploading the program against electrical damage (e.g., short-circuits). Additionally, the four large holes in the corners of the probe device 300 are mounting holes. The three un-plated holes toward the upper center will allow for non-conducting posts that prevent misorientation when mating to the device that will be programmed.

Figure 5:
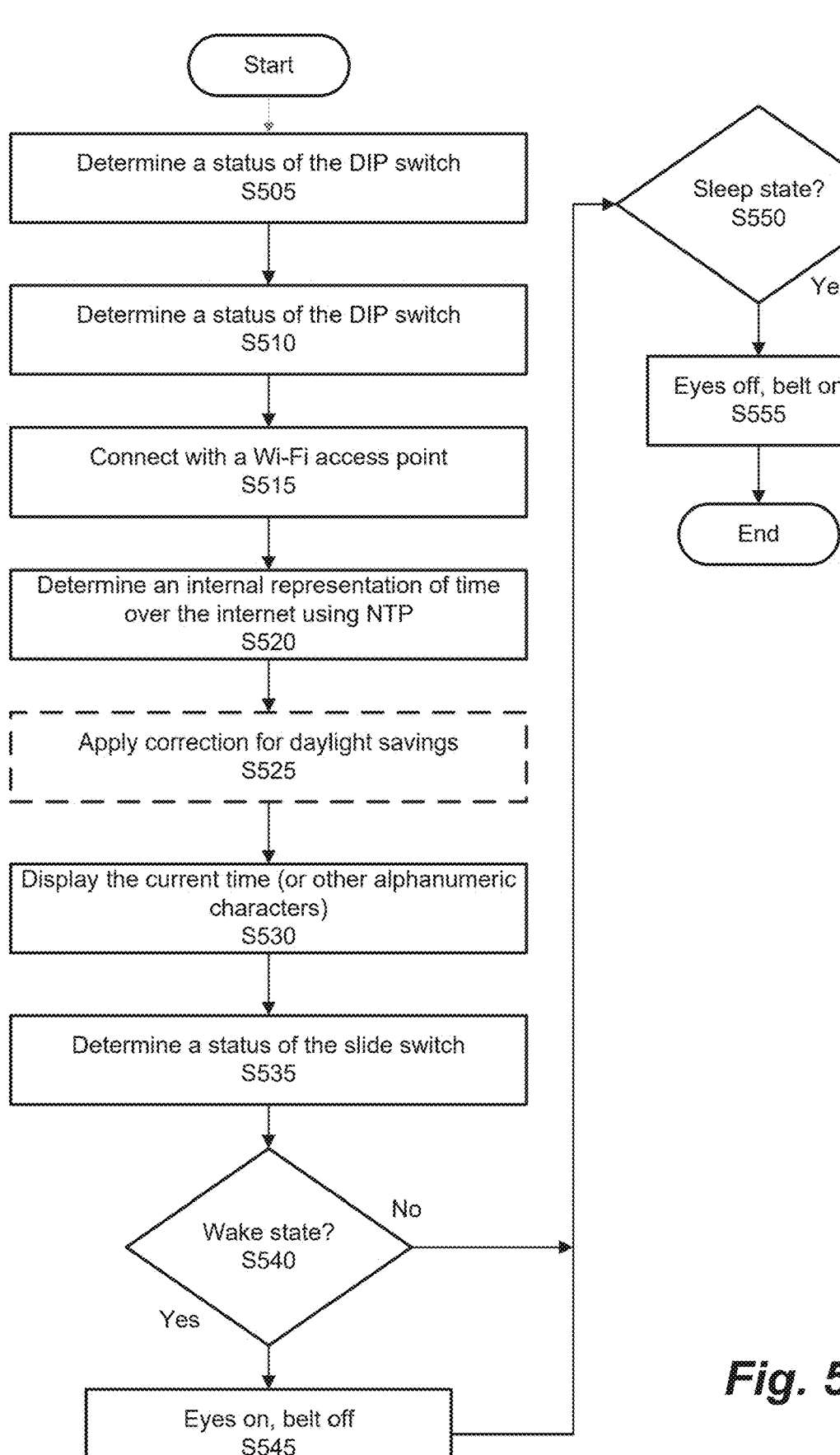
FIG. 5 is an algorithmic flow chart of a method for operating the sleep training clock 100 according to one or more aspects of the disclosed subject matter.

FIG. 5 is an algorithmic flow chart of a method for operating the sleep training clock 100 according to one or more aspects of the disclosed subject matter.

For example, the overall function of the sleep training clock 100 can be controlled by processing circuitry (e.g., firmware running on the microcontroller). In S515, the sleep training clock 100, via processing circuitry (e.g., microcontroller), can be configured to connect with a Wi-Fi access point. By connecting with a Wi-Fi access point, the sleep training clock 100 can acquire and update its internal representation of time over the internet using Network Time Protocol (NTP) (S520). Additionally, the sleep training clock 100 can get time zone information and apply appropriate corrections between the UTC time obtained over NTP and the current location, inclusive of daylight savings where appropriate (S525).

Alternatively, or additionally, the sleep training clock 100 can be configured to receive manual setting of time by a user in lieu of (or in addition to) automatically obtaining it via NTP over the internet.

The sleep training clock 100 can also be configured to securely (e.g., via https) query a remote server for firmware updates over the internet, download updates when available, and reboot to the new firmware after download. Additionally, the sleep training clock 100 can be configured to serve a set of web pages that provide information about a current status of the sleep training clock 100 and provide end-user controls for the sleep training device's configurable settings.

The sleep training clock 100 can also be configured to cause the clock face to display the current time or to display other alphanumeric characters appropriate to special situations (e.g., the user-menus driven by button presses) (S530).

Additionally, the sleep training clock 100 can be configured to sound the buzzer as an alarm based on a time selected by a user, and stop the buzzer sounding in response one of the physical buttons on the sleep training clock 100 being pushed or in response to input via the web pages that the sleep training clock 100 serves.

The sleep training clock 100 can be configured to detect a status of the slide switch, which can be used by end users to select operational mode (e.g., online or offline) (S535).

Further, the sleep training clock 100 can be configured to detect a status the DIP switch (S510), which can be used to give the robot a distinct identity (host name) on the user's network (S505). The sleep training clock 100 can also be configured to detect when either or both of the two push buttons are pressed, which drives the clock face to temporarily display alphanumeric menus or to stop an active alarm, respectively.

Additionally, the sleep training clock 100 can be configured to turn the eye and belt LEDs on and off according to firmware-defined rules (wake state in S540 and sleep state in S550). The rules can include eyes "on"/belt "off" for times when the child is allowed to leave bed (S545) and eyes "off"/belt "on" for times when the child should remain in bed (S545). In response to special states, for example a start-up sequence, the lights may be controlled separately to indicate status or error states. The lights may also be controlled to provide animations, for example at transitions between the wake and the sleep state. For example, animations can include the eyes "blinking" awake and the belt lights turning on one at a time as if the belt is circling the waist. For example, at wake, the belt can "circle" from the robot's left to right and then the eyes "blink" open. At sleep, the belt can circle from the robot's right to left, and the eyes also blink. The color of the LEDs is at all times controlled by the firmware.

Regarding client-side software, the sleep training clock 100 can be configured to serve client-side software as webpages. These webpages can run in a user's browser and provide controls by which the user can see a current configuration of the child sleep clock 100 and change the configuration. It can include HTML-based controls such as forms, text fields, and buttons. It can also include Javascript run in the browser and interacting with the device via AJAX. This software provides dynamic control of the unit.

Regarding interface design, a color of the lights can be selected. The physical LEDs used provide 256-bits of control for the precise color. The user, in the interface, is given a standard color picker input in an HTML form (<input type="color">), which gives red-blue-green values that are compatible with the 256-bit representation on the hardware. Between the processing on the client side and the server side, this form value is used to set the color of the lights. However, because the color input is standard HTML, there needs to be an internal mapping between the HTML and representations of color of the LEDs. For the client side, when the HTML form is submitted, it gets encoded by the browser as part of an HTML form submission. The value at that point is a hexadecimal representation (e.g., #ff0000 for red). That format is specified by the HTML spec.

For the server side, the server parses the hexadecimal and turns it into separate colors, one unsigned 8-bit number per color. Then that gets repackaged as a single number again, and the number gets passed into the library that controls the lights. Repackaging the value into a single number supports difference between the HTML-specified representation and the representation used by hardware. In one aspect, to get the current colors for the client (web) interface, the browser can make a call via AJAX to an endpoint on the server. For the response to communicate the colors from the device to the interface for display, the process essentially works in reverse by calling to the library to get the color data and the sending it back as the AJAX response. The main difference is that the return message from the server to the client goes as JSON, which then needs to be parsed on the client side in JavaScript so that it can be used to set elements on the interface. In other words, by recognizing that both the library and the HTML form input have 8-bit color, the common representations for the colors from both the client side and the server side can be used.

As noted earlier, the sleep training clock 100 that is connected to the Internet via Wi-Fi can periodically poll a remote server to determine if a firmware update is available. If an update is available, the sleep training clock 100 can download it from the server, install it locally, and reboot into the new firmware version. The client portion of this process is run by the sleep training clock 100 as part of its firmware. The sleep training clock 100, which acts as a client for this transaction, finds the central machine using standard domain name service (DNS) based on a server name coded into the firmware. The sleep training clock 100 accesses a specific port on the remote server and uses an SSL certificate stored on the sleep training clock 100 to validate and encrypt the transaction with the server.

In one aspect, a server (e.g., computer server 630 or web server 620) can use Apache to run the server on the centralized machine. It can be implemented as a virtual host within the Apache framework. The virtual host can be configured for https protocol only, and uses an SSL certificate compatible with the one deployed to the sleep training clock 100. A database (e.g., MySQL) can be used to keep a record of all available firmware versions and has views defined to allow the most recent version to be selected. The endpoint accessed by the client can be implemented on the server as a PHP script that reads the headers on the request from the client to determine which firmware version it currently has, queries the database to determine which version is current, and then either:

Returns a properly formatted HTTP 400 message (Bad Request) if the headers on the request do not contain specific information that validates the request as being an authentic update request from an authentic remote unit; or Returns a properly formatted HTTP 403 message (Forbidden) indicating that the server understood the request but refuses to authorize it; or Returns a properly formatted HTTP 304 message (Not Modified) to tell the client that the request was processed but no update is needed; or Returns a properly formatted HTTP 200 message (OK) with type "application/octet-stream" and payload set to the new firmware if a new firmware version is available; or Returns a properly formatted HTTP 500 message (Internal Server Error) as a last-resort failure option, for example if the MySQL query fails on the server or the firmware is not present on the filesystem to serve.

It should be appreciated that other technologies for organizing this could be used on the server side. The sleep training clock 100 can be completely decoupled from the server-side infrastructure so long as the server provides the properly formatted HTTP messages expected.

The sleep training clock 100 has various advantages. For example, there were many hurdles to overcome in designing the sleep training clock that resulted in several aspects that improve the functionality of the sleep training clock 100.

Advantages include that the firmware has been designed to allow for more control options, more sophisticated user interface in the webpages, and more robust internal mechanisms for dealing with time zones.

Additionally, the over-the-air update uses an encryption key built into the firmware to make a secure connection (e.g., https) over open internet with the update server.

Previously this had been unencrypted (http) by the endpoints and therefore restricted to operation over a VPN to prevent interception or interference.

Other aspects of the design of the sleep training clock 100 that were overcome to provide various advantages include that several of the pins must be driven to special states in order to initiate and control the programming function. As a result, this had to be considered carefully in the overall design as all pins are used to control some aspect of the device, including these pins that have special functions.

Another example includes the GPIO pin controlling the colors of the LEDs. The original design used GPIO 16 on the ESP-8266 for the control function, but, due to idiosyncrasies of the ESP-8266 this specific pin is incapable of providing the precise timing necessary for this function. This was resolved in later prototypes by remapping this function both in the traces built into the PCB 200 and in the firmware.

Additionally, as the web-based interface became more complicated, it started to be less responsive as the microcontroller was having trouble processing the server-side functions quickly enough. This was overcome through a combination of approaches. First, the individual pages were broken into pieces that could logically be served by multiple HTTP requests from the browser. For example, instead of doing all CSS inline and including the SVG code that draws the logo in each page separately, the HTML of each page references a style sheet and the SVG is loaded via an "img" tag. Although it seemed that this would create a greater load on the unit since there is some overhead to each HTTP request, it works for at least two reasons: 1. The client's browser caches some of these resources, so it reduces total traffic in a session even if it increases the traffic on the initial transactions. 2. This is more like the way modern websites are typically designed and so the browsers are optimized for it. In particular, the browser will begin rendering parts of the page while others are in transmission, so it appears more responsive to the user even if it is not in fact so as measured by total transaction time. Second, the controller was reconfigured via firmware to run at a higher clock rate.

In the above description of FIG. 5, any processes, descriptions or blocks in flowcharts can be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art. The various elements, features, and processes described herein may be used independently of one another, or may be combined in various ways. All possible combinations and sub-combinations are intended to fall within the scope of this disclosure.

The methods and systems described herein may be implemented using computer programming or engineering techniques including computer software, firmware, hardware or any combination or subset thereof.

Figure 6:
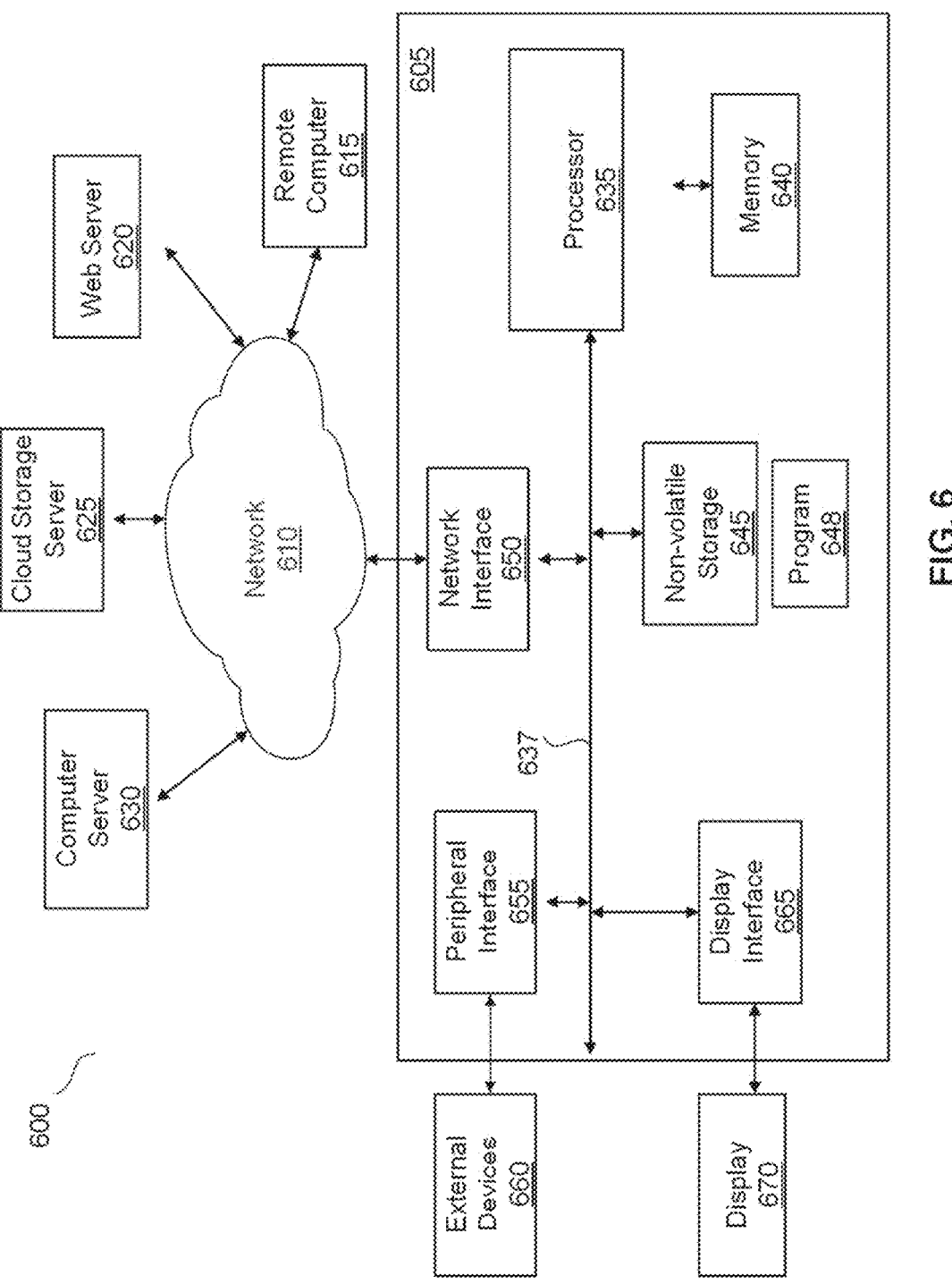
FIG. 6 is a block diagram of a computer-based system on which embodiments of the present system may be implemented.

FIG. 6 illustrates a block diagram of a computer that may implement the various embodiments described herein.

The present disclosure may be embodied as a system, a method, and/or a computer program product. The computer program product may include a computer readable storage medium on which computer readable program instructions are recorded that may cause one or more processors to carry out aspects of the embodiment.

The computer readable storage medium may be a tangible device that can store instructions for use by an instruction execution device (processor). The computer readable storage medium may be, for example, but is not limited to, an electronic storage device, a magnetic storage device, an optical storage device, an electromagnetic storage device, a semiconductor storage device, or any appropriate combination of these devices. A non-exhaustive list of more specific examples of the computer readable storage medium includes each of the following (and appropriate combinations): flexible disk, hard disk, solid-state drive (SSD), random access memory (RAM), read-only memory (ROM), erasable programmable read-only memory (EPROM or Flash), static random access memory (SRAM), compact disc (CD or CD-ROM), digital versatile disk (DVD) and memory card or stick. A computer readable storage medium, as used in this disclosure, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described in this disclosure can be downloaded to an appropriate computing or processing device from a computer readable storage medium or to an external computer or external storage device via a global network (i.e., the Internet), a local area network, a wide area network and/or a wireless network. The network may include copper transmission wires, optical communication fibers, wireless transmission, routers, firewalls, switches, gateway computers and/or edge servers. A network adapter card or network interface in each computing or processing device may receive computer readable program instructions from the network and forward the computer readable program instructions for storage in a computer readable storage medium within the computing or processing device.

Computer readable program instructions for carrying out operations of the present disclosure may include machine language instructions and/or microcode, which may be compiled or interpreted from source code written in any combination of one or more programming languages, including assembly language, Basic, Fortran, Java, JavaScript, HTML, Python, R, C, C++, C#or similar programming languages. The computer readable program instructions may execute entirely on a user's personal computer, notebook computer, tablet, or smartphone, entirely on a remote computer or compute server, or any combination of these computing devices. The remote computer or compute server may be connected to the user's device or devices through a computer network, including a local area network or a wide area network, or a global network (i.e., the Internet). In some embodiments, electronic circuitry including, for example, programmable logic circuitry, field-programmable gate arrays (FPGA), or programmable logic arrays (PLA) may execute the computer readable program instructions by using information from the computer readable program instructions to configure or customize the electronic circuitry, in order to perform aspects of the present disclosure.

Aspects of the present disclosure are described herein with reference to flow diagrams and block diagrams of methods, apparatus (systems), and computer program products according to embodiments of the disclosure. It will be understood by those skilled in the art that each block of the flow diagrams and block diagrams, and combinations of blocks in the flow diagrams and block diagrams, can be implemented by computer readable program instructions.

The computer readable program instructions that may implement the systems and methods described in this disclosure may be provided to one or more processors (and/or one or more cores within a processor) of a general purpose computer, special purpose computer, or other programmable apparatus to produce a machine, such that the instructions, which execute via the processor of the computer or other programmable apparatus, create a system for implementing the functions specified in the flow diagrams and block diagrams in the present disclosure. These computer readable program instructions may also be stored in a computer readable storage medium that can direct a computer, a programmable apparatus, and/or other devices to function in a particular manner, such that the computer readable storage medium having stored instructions is an article of manufacture including instructions which implement aspects of the functions specified in the flow diagrams and block diagrams in the present disclosure.

The computer readable program instructions may also be loaded onto a computer, other programmable apparatus, or other device to cause a series of operational steps to be performed on the computer, other programmable apparatus or other device to produce a computer implemented process, such that the instructions which execute on the computer, other programmable apparatus, or other device implement the functions specified in the flow diagrams and block diagrams in the present disclosure.

FIG. 6 is a functional block diagram illustrating a networked system 600 of one or more networked computers and servers. In an embodiment, the hardware and software environment illustrated in FIG. 6 may provide an exemplary platform for implementation of the software and/or methods according to the present disclosure.

Referring to FIG. 6, a networked system 600 may include, but is not limited to, computer 605, network 610, remote computer 615, web server 620, cloud storage server 625 and compute server 630. In some embodiments, multiple instances of one or more of the functional blocks illustrated in FIG. 6 may be employed.

Additional detail of computer 605 is shown in FIG. 6. The functional blocks illustrated within computer 605 are provided only to establish exemplary functionality and are not intended to be exhaustive. And while details are not provided for remote computer 615, web server 620, cloud storage server 625 and compute server 630, these other computers and devices may include similar functionality to that shown for computer 605.

Computer 605 may be a personal computer (PC), a desktop computer, laptop computer, tablet computer, netbook computer, a personal digital assistant (PDA), a smart phone, or any other programmable electronic device capable of communicating with other devices on network 610.

Computer 605 may include processor 635, bus 637, memory 640, non-volatile storage 645, network interface 650, peripheral interface 655 and display interface 665. Each of these functions may be implemented, in some embodiments, as individual electronic subsystems (integrated circuit chip or combination of chips and associated devices), or, in other embodiments, some combination of functions may be implemented on a single chip (sometimes called a system on chip or SoC).

Processor 635 may be one or more single or multi-chip microprocessors, such as those designed and/or manufactured by Intel Corporation, Advanced Micro Devices, Inc. (AMD), Arm Holdings (Arm), Apple Computer, etc.

Examples of microprocessors include Celeron, Pentium, Core i3, Core i5 and Core i7 from Intel Corporation; Opteron, Phenom, Athlon, Turion and Ryzen from AMD; and Cortex-A, Cortex-R and Cortex-M from Arm.

Bus 637 may be a proprietary or industry standard high-speed parallel or serial peripheral interconnect bus, such as ISA, PCI, PCI Express (PCI-e), AGP, and the like.

Memory 640 and non-volatile storage 645 may be computer-readable storage media. Memory 640 may include any suitable volatile storage devices such as Dynamic Random Access Memory (DRAM) and Static Random Access Memory (SRAM). Non-volatile storage 645 may include one or more of the following: flexible disk, hard disk, solid-state drive (SSD), read-only memory (ROM), erasable programmable read-only memory (EPROM or Flash), compact disc (CD or CD-ROM), digital versatile disk (DVD) and memory card or stick.

Program 648 may be a collection of machine readable instructions and/or data that is stored in non-volatile storage 645 and is used to create, manage and control certain software functions that are discussed in detail elsewhere in the present disclosure and illustrated in the drawings. In some embodiments, memory 640 may be considerably faster than non-volatile storage 645. In such embodiments, program 648 may be transferred from non-volatile storage 645 to memory 640 prior to execution by processor 635.

Computer 605 may be capable of communicating and interacting with other computers via network 610 through network interface 650. Network 610 may be, for example, a local area network (LAN), a wide area network (WAN) such as the Internet, or a combination of the two, and may include wired, wireless, or fiber optic connections. In general, network 610 can be any combination of connections and protocols that support communications between two or more computers and related devices.

Peripheral interface 655 may allow for input and output of data with other devices that may be connected locally with computer 605. For example, peripheral interface 655 may provide a connection to external devices 660. External devices 660 may include devices such as a keyboard, a mouse, a keypad, a touch screen, and/or other suitable input devices. External devices 660 may also include portable computer-readable storage media such as, for example, thumb drives, portable optical or magnetic disks, and memory cards. Software and data used to practice embodiments of the present disclosure, for example, program 648, may be stored on such portable computer-readable storage media. In such embodiments, software may be loaded onto non-volatile storage 645 or, alternatively, directly into memory 640 via peripheral interface 655. Peripheral interface 655 may use an industry standard connection, such as RS-232 or Universal Serial Bus (USB), to connect with external devices 660.

Display interface 665 may connect computer 605 to display 670. Display 670 may be used, in some embodiments, to present a command line or graphical user interface to a user of computer 605. In one aspect, the display 670 can digitally display digits for a clock, for example. Display interface 665 may connect to display 670 using one or more proprietary or industry standard connections, such as VGA, DVI, DisplayPort and HDMI.

As described above, network interface 650, provides for communications with other computing and storage systems or devices external to computer 605. Software programs and data discussed herein may be downloaded from, for example, remote computer 615, web server 620, cloud storage server 625 and compute server 630 to non-volatile storage 645 through network interface 650 and network 610. Furthermore, the systems and methods described in this disclosure may be executed by one or more computers connected to computer 605 through network interface 650 and network 610. For example, in some embodiments the systems and methods described in this disclosure may be executed by remote computer 615, computer server 630, or a combination of the interconnected computers on network 610.

Data, datasets and/or databases employed in embodiments of the systems and methods described in this disclosure may be stored and or downloaded from remote computer 615, web server 620, cloud storage server 625 and compute server 630.

Figure 7A:
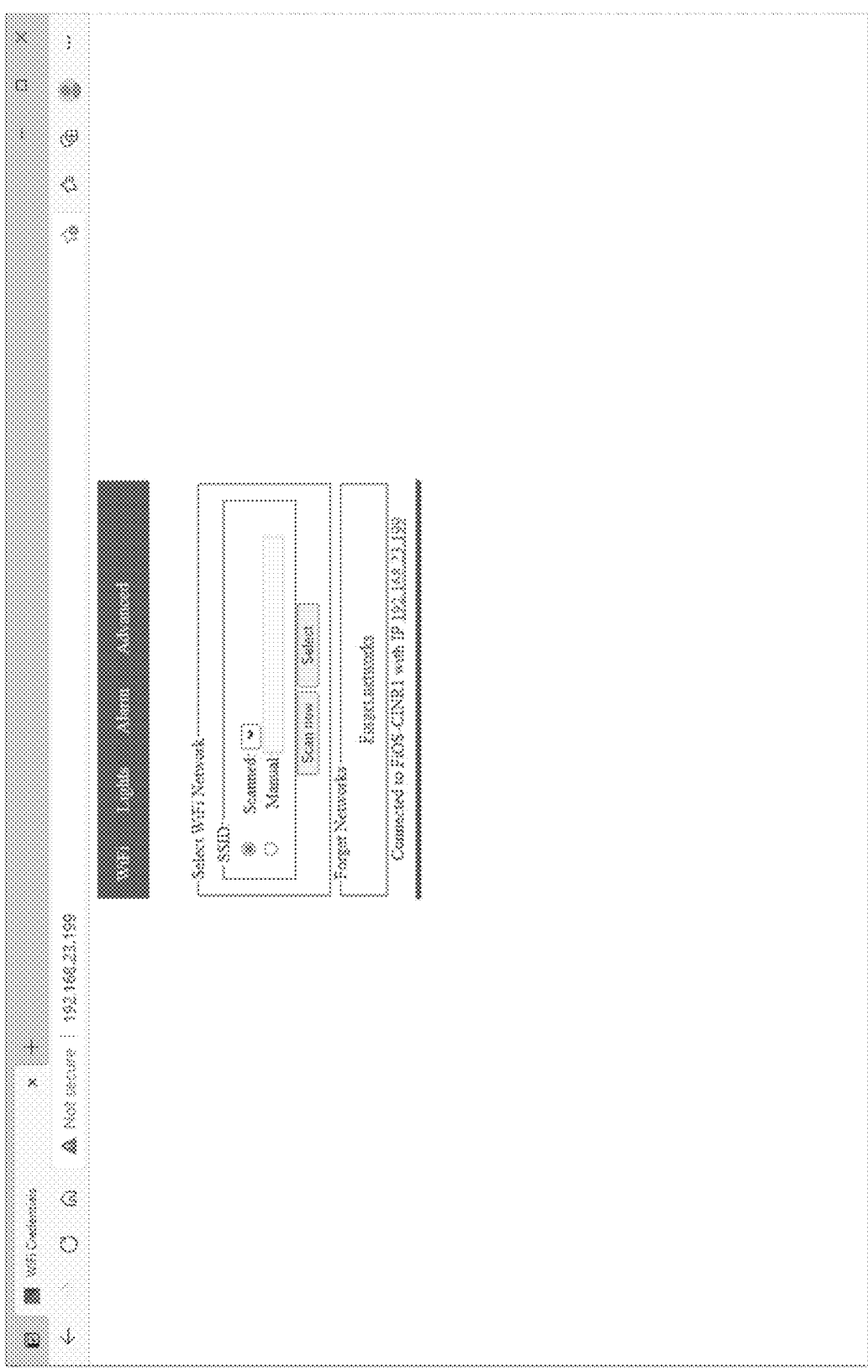
FIG. 7A illustrates an exemplary user interface for selecting a Wi-Fi network for the sleep training clock according to one or more aspects of the disclosed subject matter.

FIG. 7A illustrates an exemplary user interface 700 for selecting a Wi-Fi network for the sleep training clock 100 according to one or more aspects of the disclosed subject matter. For example, a user can interact with the user interface 700 to select a Wi-Fi network, scan for networks, forget networks, and the like.

Figure 7B:
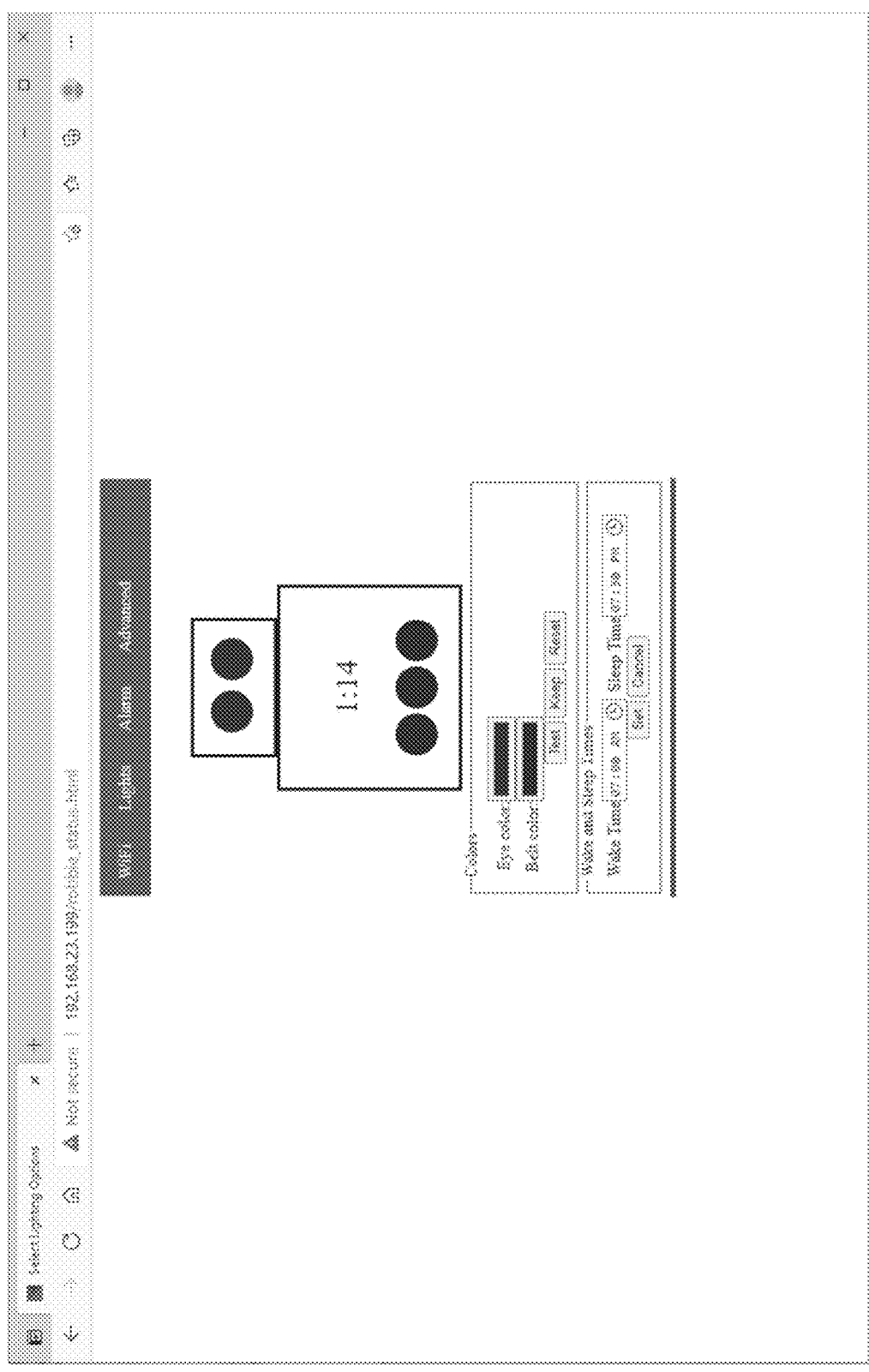
FIG. 7B illustrates an exemplary user interface for managing the lights of the sleep training clock according to one or more aspects of the disclosed subject matter.

FIG. 7B illustrates an exemplary user interface 705 for managing the lights 110a,b and 115a-c of the sleep training clock 100 according to one or more aspects of the disclosed subject matter. For example, a user can interact with the user interface 705 to set the color of the LEDs for the eyes and belt, set and/or adjust wake and sleep times, and the like.

Figure 7C:
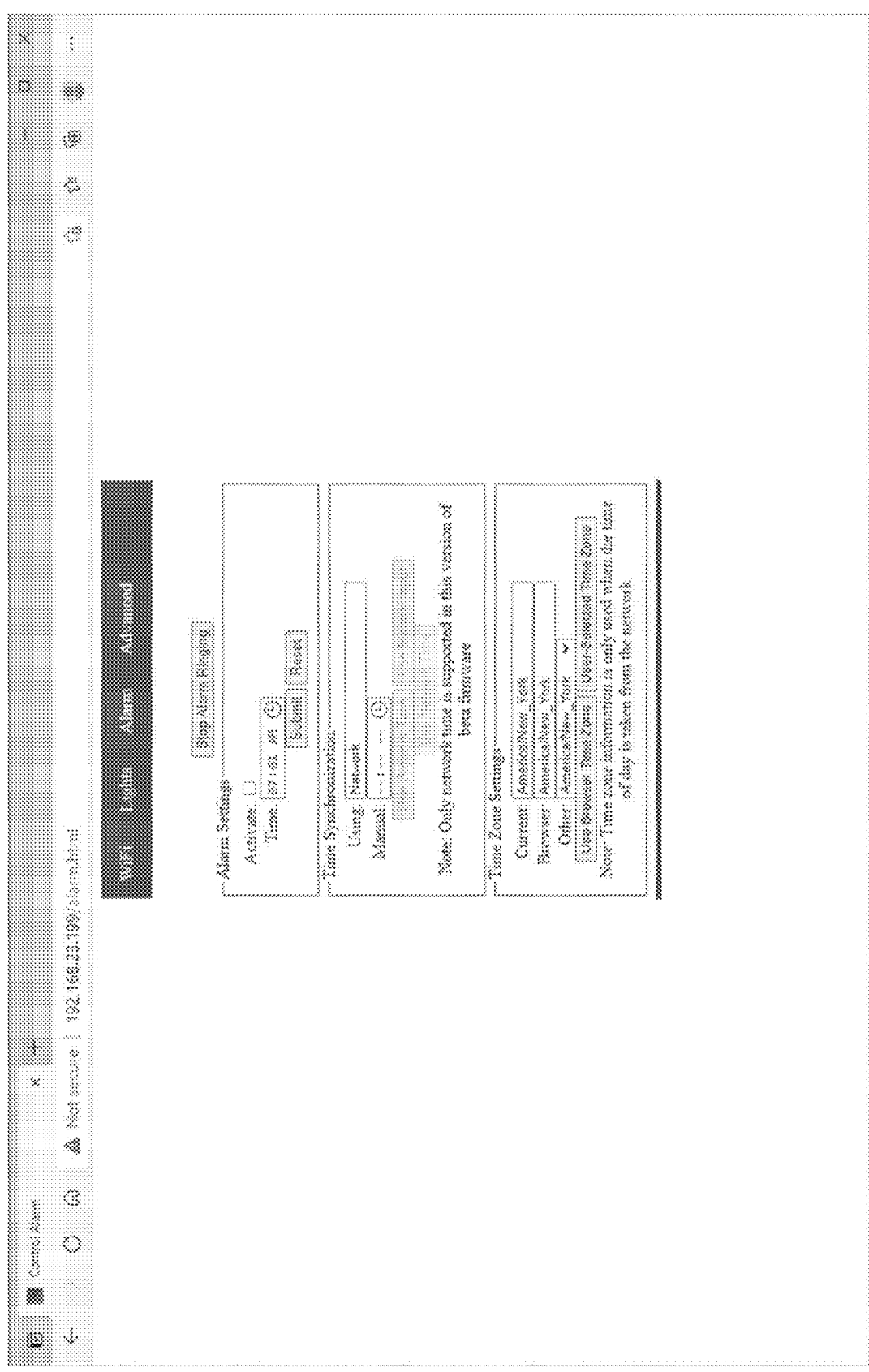
FIG. 7C illustrates an exemplary user interface for managing the alarm of the sleep training clock according to one or more aspects of the disclosed subject matter.

FIG. 7C illustrates an exemplary user interface 710 for managing an alarm of the sleep training clock 100 according to one or more aspects of the disclosed subject matter. For example, the user can interact with the user interface 710 to set a time for an alarm, activate the alarm, stop the alarm from going off, synchronize the time, set a time zone, and the like.

Figure 7D:
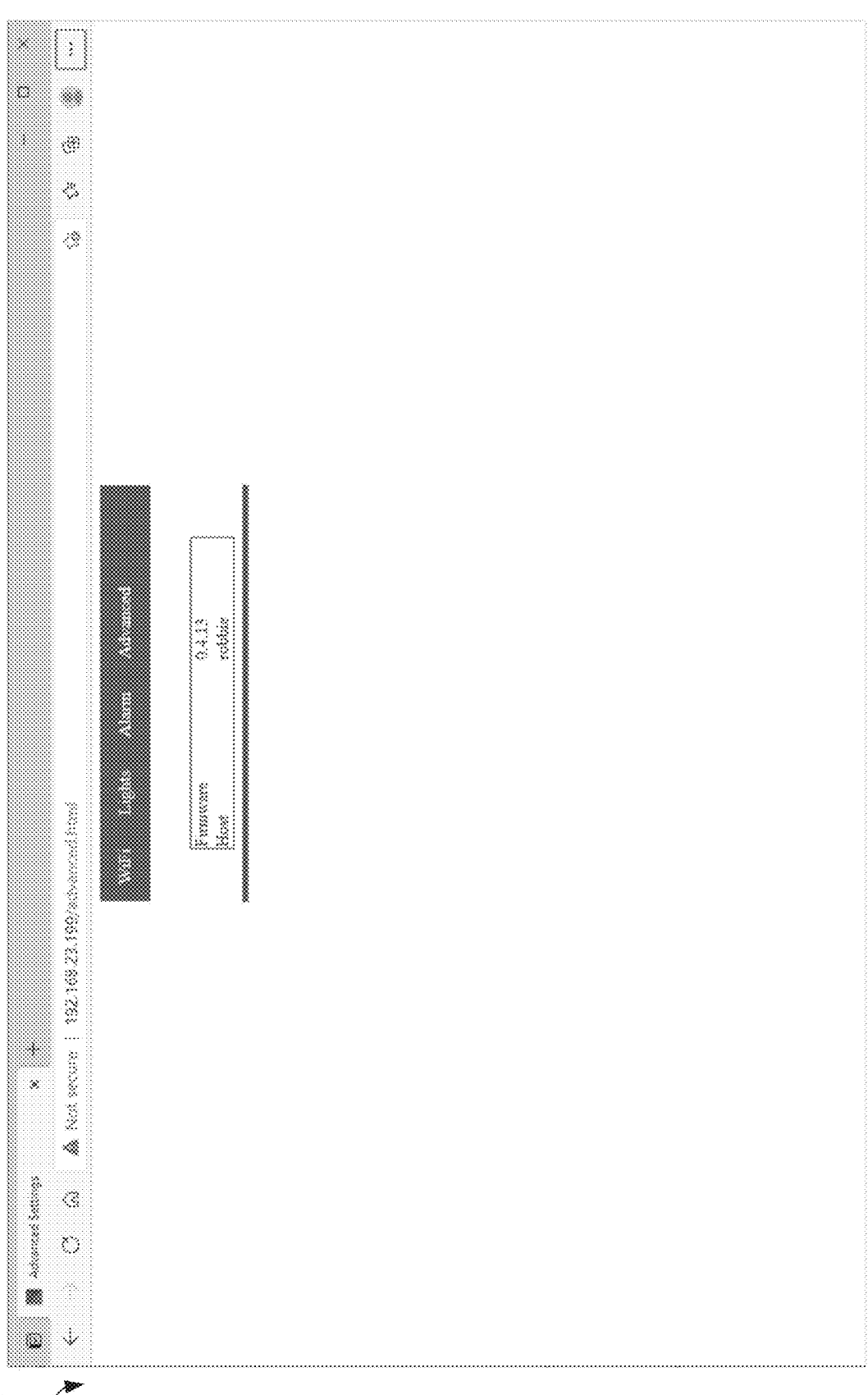
FIG. 7D illustrates an exemplary user interface for viewing and/or managing advanced features of the sleep training clock according to one or more aspects of the disclosed subject matter.

FIG. 7D illustrates an exemplary user interface 715 for viewing and/or managing advanced features of the sleep training clock according to one or more aspects of the disclosed subject matter. For example, the user can interact with the user interface 715 to view firmware information, host information, and the like.

Obviously, numerous modifications and variations of the present invention are possible in light of the above teachings. It is therefore to be understood that within the scope of the appended claims, the invention may be practiced otherwise than as specifically described herein.

The invention claimed is:

1. An electronic device, comprising:
   a body shaped like a robot including a face, a torso, and two legs;
   five light emitting diodes (LEDs), wherein two of the LEDs are disposed in the face and three LEDs are disposed in the torso;
   a digital clock face disposed in the torso;
   a printed circuit board (PCB); and
   circuitry configured to perform sleep training, wherein the circuitry for performing sleep training is configured to:
   display a time on the digital clock face,
   determine whether the electronic device is in a wake state based on the time,
   based on the determination that the electronic device is in the wake state, turn on the two LEDs disposed in the face and turn off the three LEDs disposed in the torso,
   determine whether the electronic device is in a sleep state based on the time, and based on the determination that the electronic device is in the sleep state, turn off the two LEDs disposed in the face and turn on the three LEDs disposed in the torso, wherein the PCB includes a programming port configured to allow a temporary physical connection to be made between the PCB, including components mounted on the PCB, and an external computer, wherein the programming port is configured to receive a probe device that mates with the programming port, wherein the probe device includes a PCB to which six pins are attached to make temporary contact with corresponding locations on the programming port, and wherein the programming port is configured to receive three non-conducting pegs of larger diameter attached to the probe device that fit into corresponding holes in the programming port, wherein the six pins and three pegs are arranged in a 3×3 pattern with the pegs taking positions that only allow the probe to mate with the programming port from one side of the board and in one direction.

2. The electronic device of claim 1, wherein the circuitry is further configured to connect to a wi-fi access point.

3. The electronic device of claim 2, wherein the circuitry is further configured to acquire and update an internal representation of time over an internet using network time protocol (NTP), and apply a time zone correction between a time acquired over NTP and a current location of the electronic device.

4. The electronic device of claim 3, wherein the circuitry is further configured to display a current time on the digital clock face.

5. The electronic device of claim 2, wherein the circuitry is further configured to securely query a remote server for firmware updates over an internet, download updates based on availability, and reboot to the updated firmware after download.

6. The electronic device of claim 2, wherein the circuitry is further configured to serve a set of web pages that provide information about a status of the electronic device, and provide end-user controls for configurable settings of the electronic device.

7. The electronic device of claim 6, wherein the circuitry is further configured to turn off an alarm prompted by user input via the set of web pages served by the electronic device.

8. The electronic device of claim 1, wherein the circuitry is further configured to display alphanumeric characters on the digital clock face based on user input including user-menus driven by one or more button presses.

9. The electronic device of claim 1, wherein the circuitry is further configured to determine a status of a slide switch, wherein the slide switch is configured to be operated by a user to select an operational mode of the electronic device.

10. The electronic device of claim 1, wherein the circuitry is further configured to determine a status of a dual in-line package (DIP) switch, wherein the DIP switch is configured to be operated by a user to give the electronic device a distinct identity on a network.

11. The electronic device of claim 1, wherein the circuitry is further configured to animate one or more of the LEDs during a transition between the sleep state and the wake state.

12. The electronic device of claim 11, wherein the circuitry is further configured to animate the two LEDs disposed in the face to blink based on transitioning from the sleep state to the wake state.

13. The electronic device of claim 1, wherein the circuitry is further configured to animate one or more of the LEDs during a transition between the wake state and the sleep state.

14. The electronic device of claim 1, wherein the circuitry is further configured to animate the three LEDs disposed in the torso to illuminate one at a time in a predetermined direction as if the LEDs are circling the torso based on transitioning from the wake state to the sleep state.

15. The electronic device of claim 1, wherein the pegs of the probe device are longer than the pins.

* * * * *